United States Patent [19]

Clemence et al.

[11] Patent Number: 4,988,727
[45] Date of Patent: Jan. 29, 1991

[54] N-(AMINOINDANYL)AMIDES AS ANALGESICS AND ANTIARRHYTHMICS

[75] Inventors: François Clemence; Michel Fortin, both of Paris, France

[73] Assignee: Roussel Uclaf, Paris, France

[21] Appl. No.: 409,048

[22] Filed: Sep. 19, 1989

Related U.S. Application Data

[62] Division of Ser. No. 136,814, Dec. 22, 1987, Pat. No. 4,888,355.

[30] Foreign Application Priority Data

Dec. 23, 1986 [FR] France ................... 86 1802

[51] Int. Cl.$^5$ ............... A61K 31/40; A61K 31/38; A61K 31/335; A61K 31/495; C07D 405/10; C07D 401/10; C07D 407/10
[52] U.S. Cl. ................... 514/422; 514/231.5; 514/233.5; 514/252; 514/253; 514/320; 514/324; 514/326; 514/438; 514/443; 514/469; 544/145; 544/146; 544/152; 544/153; 544/170; 544/175; 544/376; 544/379; 546/196; 546/202; 546/207; 546/212; 546/213; 546/214; 548/517; 548/525; 548/527; 549/57; 549/58; 549/62; 549/65; 549/68; 549/70; 549/78; 549/468; 549/471
[58] Field of Search ............... 544/145, 146, 152, 153, 544/376, 379; 546/196, 202, 207, 212, 213, 214; 548/517, 525, 527; 549/57, 58, 62, 65, 68; 514/231.5, 233.5, 252, 253, 320, 324, 326, 422, 438, 443, 469

[56] References Cited

PUBLICATIONS

Clemence et al., Chem. Abst. 109-149341p (1988).

Primary Examiner—Cecilia Shen
Attorney, Agent, or Firm—Bierman and Muserlian

[57] ABSTRACT

A compound selected from the group consisting of all enantiomeric and diastereoisomeric forms possible of compounds of the formula

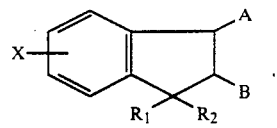

wherein X is selected from the group consisting of hydrogen, halogen, and alkyl and alkoxy of 1 to 5 carbon atoms, $R_1$ and $R_2$ are individually selected from the group consisting of hydrogen and alkyl of 1 to 5 carbon atoms, one of A and B being

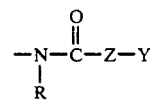

and the other being

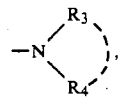

R is hydrogen or alkyl of 1 to 5 carbon atoms, Z is —(CH$_2$)$_n$— or branched alkylene of 2 to 8 carbon atoms, n is an integer from 0 to 5, Y is selected from the group consisting of naphthyl, indenyl, heterobicyclics and heteromonocyclic containing 5 to 6 ring members, all optionally substituted with at least one member of the group consisting of alkyl and alkoxy of 1 to 5 carbon atoms, halogen, —OH, —CF$_3$, —NO$_2$, —NH$_2$ monoalkylamino and dialkylamino of 1 to 4 alkyl carbon atoms and phenyl optionally substituted with at least one member of the group consisting of halogen and alkyl and alkoxy of 1 to 4 carbon atoms, $R_3$ and $R_4$ are individually hydrogen or alkyl or 1 to 5 carbon atoms or taken together with the nitrogen form a heterocyclic of 5 to 6 ring members and optionally containing —O—, —S— or nitrogen in the ring and their non-toxic, pharmaceutically acceptable acid addition salts having central analgesic and antiarythmic activity among other activities.

16 Claims, No Drawings

N-(AMINOINDANYL)AMIDES AS ANALGESICS AND ANTIARRHYTHMICS

PRIOR APPLICATION

This application is a division of U.S. Pat. application Ser. No. 136,814 filed Dec. 22, 1987, now U.S. Pat. No. 4,888,355.

STATE OF THE ART

Relevant prior art includes European patent applications No. 0,147,085 and No. 0,108,602.

OBJECTS OF THE INVENTION

It is an object of the invention to provide the novel compounds of formula I and their non-toxic, pharmaceutically acceptable acid addition salts and a process for their preparations.

It is another object of the invention to provide novel analgesic compositions and a novel method of relieving pain in warm-blooded animals.

These and other objects and advantages of the invention will become obvious from the following detailed description.

THE INVENTION

The novel compounds of the invention are selected from the group consisting of all enantiomeric and diastereoisomeric forms possible of compounds of the formula

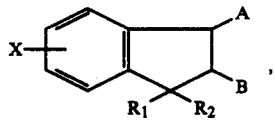

wherein X is selected from the group consisting of hydrogen, halogen, and alkyl and alkoxy of 1 to 5 carbon atoms, $R_1$ and $R_2$ are individually selected from the group consisting of hydrogen and alkyl of 1 to 5 carbon atoms, one of A and B being

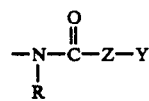

and the other being

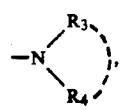

R is hydrogen or alkyl of 1 to 5 carbon atoms, Z is $-(CH_2)_n-$ or branched alkylene of 2 to 8 carbon atoms, n is an integer from 0 to 5, Y is selected from the group consisting of naphthyl, indenyl, heterobicyclics and heteromonocyclic containing 5 to 6 ring members all optionally substituted with at least one member of the group consisting of alkyl and alkoxy of 1 to 5 carbon atoms, halogen, $-OH$, $-CF_3$, $-NO_2$, $-NH_2$ monoalkylamino and dialkylamino of 1 to 4 alkyl carbon atoms and phenyl optionally substituted with at least one member of the group consisting of halogen and alkyl and alkoxy of 1 to 4 carbon atoms, $R_3$ and $R_4$ are individually hydrogen or alkyl of 1 to 5 carbon atoms or taken together with the nitrogen form a heterocyclic of 5 to 6 ring members and optionally containing $-O-$, $-S-$ or nitrogen in the ring and their non-toxic, pharmaceutically acceptable acid addition salts.

When X, R, $R_2$, $R_1$, $R_3$ and $R_4$ are alkyl, they are preferably methyl, ethyl, n-propyl or isopropyl but they also may be n-butyl, isobutyl or n-pentyl. When X is halogen, it is preferably chlorine but it may also be fluorine, bromine or iodine. When X is alkoxy, it may be n-propoxy, isopropoxy, n-butoxy, sec.-butoxy or tert.-butoxy, but it is preferably methoxy or ethoxy.

When Z is $-(CH_2)_n-$, n is preferably 0 to 1 and when Z is a branched alkylene, it is preferably substituted by at least one methyl or ethyl and examples are 1,1-ethanediyl, 1-methyl-1,2-ethanediyl, 1 or 2-methyl-, 1,2-propanediyl and 1-ethyl-1,2-ethanediyl.

When Y is a monoheterocyclic of 5 to 6 ring members, it is preferably thiazolyl, pyridinyl, oxazolyl, isoxazolyl, imidazolyl, or thienyl. When Y is heterocyclic, it is preferably indolyl, quinolyl, benzofuranyl, benzo[b]thienyl, benzimidazolyl, benzoxazolyl or benzothiazolyl.

When Y is substituted naphthyl, indenyl or mono or biheterocyclic the substituents are preferably one or two members selected from the group consisting of methyl, ethyl, methoxy, ethoxy, chlorine, bromine, fluorine, $-NO_2$, $-CF_3$ and phenyl. When the substituents are mono- or dialkylamino, the alkyls are preferably methyl or ethyl. When the phenyl is substituted, the substituents are preferably one or two members of the group consisting of methyl, ethyl, methoxy, ethoxy, chlorine, bromine or fluorine.

When $R_3$ and $R_4$ together with the nitrogen atoms form a heterocyclic it is preferably pyrrolidinyl, piperazinyl, piperidinyl or morpholinyl.

Examples of suitable acids for the preparation of the non-toxic, pharmaceutically acceptable acid addition salts are inorganic acids such as hydrochloric acid, hydrobromic acid, nitric acid, sulfuric acid and phosphoric acid and organic acids such as formic acid, acetic acid, propionic acid, maleic acid, fumaric acid, succinic acid, tartaric acid citric acid, oxalic acid, glyoxylic acid and aspartic acid, alkane sulfonic acids such as methane sulfonic acid, aryl sulfonic acids such as benzene sulfonic acid and aromatic carboxylic acids such as benzoic acid.

Among the preferred compounds of formula I are those wherein A and B have the trans configuration, those wherein in the group

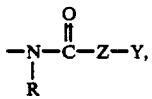

R is hydrogen, methyl or ethyl, Z is $-CH_2-$ or

Y is naphthyl, indenyl, benzo[b]thienyl, indolyl, benzofuranyl, quinolyl, benzimidazolyl, benzoxazolyl, benzothiazolyl and thienyl optionally substituted with phenyl and those wherein X, $R_1$ and $R_2$ are hydrogen and

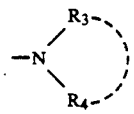 is pyrrolidinyl and their non-toxic, pharmaceutically acceptable acid addition salts.

Specific preferred compounds of formula I are (trans)(±) N-[2,3-dihydro-2-(1-pyrrolidinyl-1H-inden-1-yl]-N-methyl-4-benzo[b]thiopheneacetamide and (trans)(±) N-[2,3-dihydro-2-(1-pyrrolidinyl)-1H-inden-1-yl]-N-methyl-1-naphtalene-acetamide and their acid addition salts.

The novel process of the invention for the preparation of compounds of formula I wherein A and B have the trans configuration comprises condensing a compound of the formula

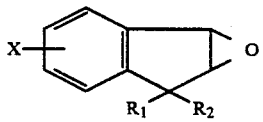

wherein X, $R_1$ and $R_2$ have the above definitions with either an amine of the formula

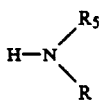

wherein R has the above definitions and $R_5$ is an amine protecting group, especially benzyl, to obtain a compound of the formula

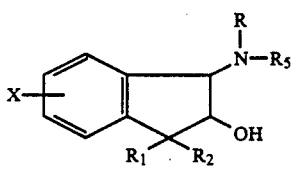

and condensing the activated hydroxyl with an amine of the formula

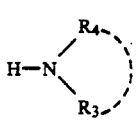

wherein $R_3$ and $R_4$ have the above definitions to obtain a compound of the formula

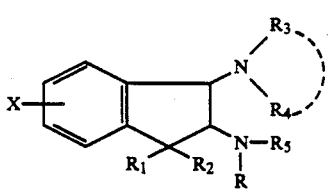

then eliminating the protective group $R_5$ to obtain a compound of the formula

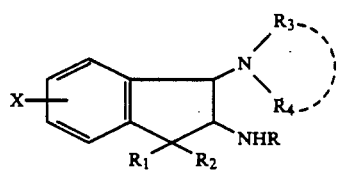

treating the latter with an acid of the formula $$Y-Z-COOH \qquad (VIII)$$

or a functional derivative thereof to obtain a compound of formula I when A is

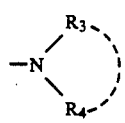

and B is

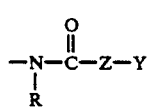

or with an amine of formula V to obtain a compound of the formula

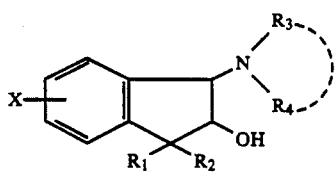

and reacting the active hydroxyl with an amine of the formula $$R-NH_2 \qquad (X)$$

wherein R has the above definitions to obtain a compound of the formula

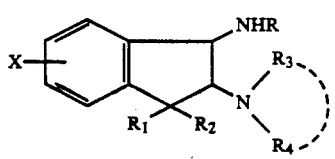

and condensing the latter with an acid of formula VIII or a functional derivative thereof to obtain the corresponding compound of formula I when A is

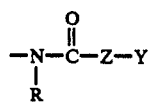

and B is

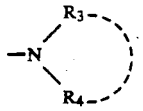

which may be resolved to obtain the optically active isomers and treated with an acid to form the acid addition salts.

In a preferred mode of the process of the invention, the hydroxyl of the compound of formulae IV and IX is activated with methane sulfonyl chloride and the protective group $R_5$ is removed from the compound of formula VI by hydrogeneration in the presence of a palladium catalyst. The activation of the hydroxyl group of a compound of formula VIII is effected with carbonyldiimidazole or with an acid chloride or mixed anhydride. The compounds of formula I may be resolved by known methods.

The compounds of formula I wherein A and B have the cis configuration may be prepared as follows

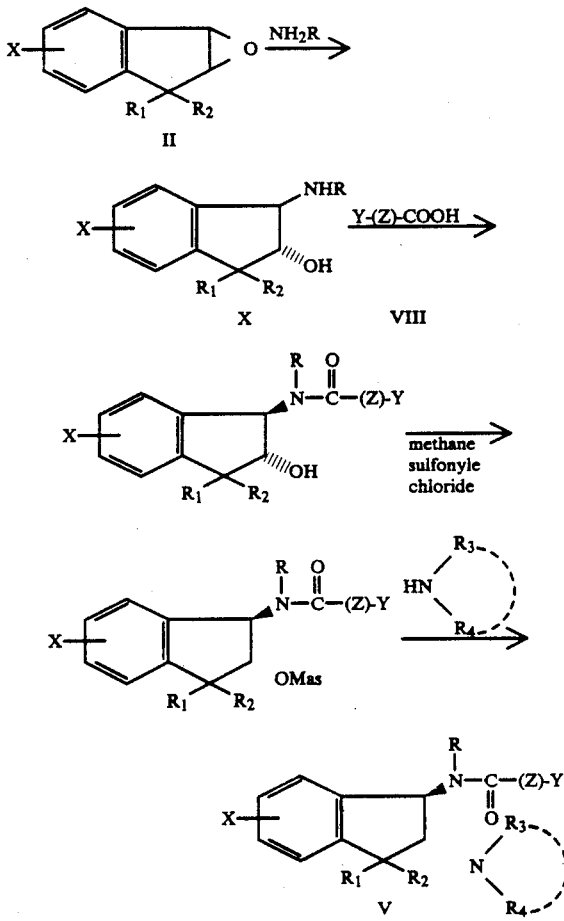

The antiarythmic compositions of the invention are comprised of an antiarythmically effective amount of at least one compound of formula I and their non-toxic, pharmaceutically acceptable acid addition salts and an inert pharmaceutical carrier or excipient. The compositions may be in the form of tablets, dragees, gelules, granules, suppositories, creams, gels, pommades, injectable solutions or suspensions or in aerosols.

In addition to the antiarythmic activity, the compounds of formula I and their salts also have a strong affinity for opiate receptors, especially Kappa receptors and have central analgesic properties. The compounds also possess diuretic, cerebral antiischemic and hypotensive activity.

The compositions of the invention may be used to relieve pain of any origin such as pain of a muscular, nervous or articular nature. They may be used to treat toothaches, migraines, zona in the treatment of intense pain, especially sensitive to peripherical antalgics such as in the course of nephretic or biliary colics pancreatitis, neoplasic processes and in the treatment of post operative and post-traumatic pains.

The compounds of the invention may be used for the treatment of edemateous syndromes, cardiac insufficiences, certain obesities, cirrhosis, in the treatment of severe and resistant edemas, particularly those of congestive cardiac insufficiencies and prolonged treatment of arterial hypertension.

Examples of suitable excipients are talc, arabic gum, lactose, starch, magnesium stearate, cocoa butter, aqueous or non-aqueous vehicles fatty bodies of animal or vegetable origin, parafinic derivatives, glycol diverse wetting agents, dispersants and emulsifiers and preservatives.

The novel method of the invention for inducing antiarythmic activity in warm-blooded animals, including humans, comprises administering to warm-blooded animals an antiarythmically effective amount of at least one compound of formula I and its non-toxic, pharmaceutically acceptable acid addition salts. The compounds may be administered oral rectally parenterally or topically on the skin or mucosae and the usual daily dose is 0.07 to 6 mg/kg depending on the condition treated, the specific compound and the method of administration. For example, for the treatment of supraventricular and junctional and ventricular arythmia, the compounds may be orally administered at 3 to 12 mg/kg and for analgesic activity, the daily dose is 0.3 to 6 mg/kg when administered orally, and 0.07 to 1.5 mg/kg when administered parenterally.

The compounds of formulae IV, VI, VII, IX and XI in which X is not hydrogen are novel intermediate products.

In the following examples there are described several preferred embodiments to illustrate the invention. However, it is to be understood that the invention is not intended to be limited to the specific embodiments.

EXAMPLE 1

Trans (+) N-[2,3-dihydro-2-(pyrrolidin-1-yl)-1H-inden-1-yl]-N-methyl-4-benzo[b]thiophene-acetamide

STEP A: Trans (±) 2,3-dihydro-1-(pyrrolidin-1-yl)-1H-inden-2-ol

A solution of 10.8 ml of pyrrolidine in 6.75 g of 2,3-epoxy-indane [described by Mousseron et al, Bull. de Soc. Chim. de France, 1946, p. 629–630] was slowly added to 10.8 ml of decentralized water and after increasing the temperature to 65° C., the mixture was stirred for 90 minutes at 65° C. 20 ml of demineralized water were then added and excess pyrrolidine was distilled off at reduced pressure to obtain an oil phase and an aqueouse phase. The aqueouse phase was saturated with sodium chloride and 1 ml of 32% sodium hydroxide was added thereto. The mixture was extacted with ether and the ether phase was dried and evaporated to dryness under reduced pressure. The oil residue was chromatographed over silica and eluted with ethyl acetate containing 5% of triethylamine to obtain 8.81 g of trans (±) 2,3-dihydro-1-(pyrrolidin-1-yl)-1H-inden-2-ol.

STEP B: Trans (±) 2,3-dihydro-N-methyl-2-(pyrrolidin-1-yl)-1H-inden-1-amine

A mixture of 8.71 g of the product of Step A, 87 ml of methylene chloride and 13.8 ml of triethylamine was cooled to −20° C. and a solution of 6.6 ml of methane sulfonyl chloride and 8.7 ml of methylene chloride was added thereto at −20° C. After stirring at −20° C. for 20 minutes, the temperature rose to 0° C. and the mixture was washed with iced water. The wash water was extracted with methylene chloride and the organic phase was dried and evaporated to dryness under reduced pressure to obtain 13.36 g of resin which was the trans (±) methane sulfonate of 2,3-dihydro-1-(pyrrolidin-1-yl)-1H-inden-2-ol. The residue was treated in an autoclave with an aqueous solution of 35–40% of methylamine by heating at 80° C. for 20 hours (pressure stabilized at 3 bar) and after cooling to 20° C., the mixture was taken up in 100 ml of ether. The mixture was saturated with sodium chloride and the decanted organic phase was washed with water saturated with sodium chloride, dried and treated with activated carbon. The mixture was filtered and rinsed and the filtrate was evaporated to dryness under reduced pressure to obtain 6.98 g of a resin which was chromatographed over silica and eluted with a 85-10-5 mixture of ethyl acetate-methanol-triethylamine to obtain 3.71 g of trans (±) 2,3-dihydro-N-methyl-2-(pyrrolidin-1-yl)-1H-inden-1-amine.

STEP C: Trans (±) N-[2,3-dihydro-2-(pyrrolidin-1-yl)-1H-inden-1-yl]-N-methyl-4-benzo[b]thiophene-acetamide A mixture of 0.5 g of 4-thianaphthene-acetic acid, 0.422 g of carbonyldimmidazole and 20 ml of tetrahydrofuran was stirred for one hour and then a solution of 0.432 g of the product of Step B in 5 ml of tetrahydrofuran was slowly added thereto. The mixture was stirred for 3½ hours and the tetrahydrofuran was distilled off under reduced pressure. The residue was taken up in 100 ml of ether and the solution was washed with aqueous saturated sodium bicarbonate solution, then with aqueous saturated sodium chloride solution, dried and evaporated to dryness under reduced pressure to obtain 0.61 g of trans (±)- N-[2,3-dihydro-2-(pyrrolidin-1-yl)-1H-inden-1-yl]-N-methyl-4-benzo[b]thiophene-acetamide in the form of an oil.

0.405 g of the product were dissolved at 50° C. in 4 ml of 99% ethanol and 0.5 ml of hot 5.75 N hydrogen chloride in ethanol were added thereto. The mixture was filtered hot and the filter was rinsed with ethanol at 50° C. Crystallization was induced at 30° C. and the mixture was allowed to stand at 20° C. for 2 hours and was then vacuum filtered. The product was rinsed with ethanol, then with ether and dried to obtain 0.150 g of the hydrochloride melting at 192° C.

EXAMPLE 2

Trans (±) N-[2,3-dihydro-2-(1-pyrrolidinyl-1H-inden-1-yl]-N-methyl-5-phenyl-2-thiophene-acetamide Using the procedure of Step C of Example 1, 0.432 g of the product of Step B of Example 1, 0.567 g of 5-phenyl-2-thiophene-acetic acid and 0.422 g of carbonyldiimidazole were reacted to obtain 0.571 g of trans-(±)-N-[2,3-dihydro-2-(1-pyrrolidinyl)-1H-inden-1-yl]-N-methyl-5-phenyl-2-thiophene-acetamide and then 0.457 g of its hydrochloride melting at ≃249° C.

Analysis: $C_{26}H_{28}N_2OS \cdot HCL$; molecular weight=453.05;
Calculated: %C 68.93, %H 6.45, %N 6.18, %S 7.08, %C 7.82;
Found: 69.2. 6.5. 6.2. 7.0. 8.1.

EXAMPLE 3

1-pyrrolidinyl)-1H-inden-1-yl]-N-methyl-1-naphthalene-acetamide

Using the procedure of Step C of Example 1, 0.432 g of the product of the product of Step B of Example 1, 0.484 g of 1-naphthylacetic acid and 0.422 g of carbonyldiimidazole were reacted to obtain 0.718 g of trans (+) N-[2,3-dihydro-2-(1-pyrrolidinyl)-1H-inden-1-yl]-N-methyl-1-naphthalene-acetamide melting at 127° C. and then 0.655 g of the base were reacted to obtain 0.533 g of its hydrochloride melting at ≃240° C.

Analysis: $C_{26}H_{28}N_2O \cdot HCl$; molecular weight=420.986;
Calculated: %C 74.18, %H 6.94, %N 6.65, %Cl 8.42;
Found: 74.2. 7.1. 6.8. 8.3.

EXAMPLE 4

Trans (±) N-[2,3-dihydro-2-(1-pyrrolidinyl)-1H-inden-1-yl]-N-methyl-2-naphthalene-acetamide Using the procedure of Example 3, 2-naphthyl-acetic acid was reacted to obtain 0.805 g of trans (±) N-[2,3-dihydro-2-(1-pyrrolidinyl) -1H-inden-1-yl]-N-methyl-2-naphthalene-acetamide hydrochloride which melted at 255° C. after crystallization from isopropanol.

Analysis: $C_{26}H_{28}N_2O \cdot HCl$ ; molecular weight=420.986;
Calculated: %C 74.18, %H 6.94 ,%N 6.65, %Cl 8.42;
Found: 74.4. 7.0. 6.5. 8.6.

EXAMPLE 5

Using the procedure of Example 3, the maleate of trans (±) N-[2,3-dihydro-2-(1-pyrrolidinyl)-1H-inden-1-yl]-N-methyl-1H-indol-4-acetamide melting at 202°-204° C. was prepared.

EXAMPLE 6

Tablets were prepared containing 200 mg of the compound of Example 1 and sufficient excipient of lactose, starch, talc and magnesium stearate to obtain tablets weighing 800 mg.

An injectable solution was prepared containing 50 mg of the product of Example 1 and sufficient sterile solvent for a final volume of 5 ml.

PHARMACOLOGICAL DATA

A. In vitro bonding of Kappa opiate receptor

Membrane culots preserved at −30° C. for about 30 days and prepared from guinea pig cerebellum were suspended in buffered Tris pH of 7.7. 2 ml fractions were placed in hemolysis tubes and 1 nM of $9^3H$ ethylketocyclazocine and $5\times10^{-6}M$ of test compound were added thereto (in triple) When the test product displaced more than 50% of the radioactivity tied specifically to the receptor, the test was repeated with a range of seven doses to determine the dose which inhibited by 50% the radioactivity tied specifically to the receptor which is deemed $CI_{50}$ The non-specific bond was determined by the addition of the known product, U-50488 H [Lahti et al, Life Science, Vol. 31 (1982), p 2257], at $10^{-5}M$ (in triple). The mixture was incubated at 25° C. for 40 minutes, placed in a bath at 0° C. for 5 minutes and vacuum filtered. The product was rinsed with buffered Tris at a pH of 7.7 and the radioactivity was counted in the presence of Trition scintillation. The results were expressed directly as the 50% inhibiting concentration ($CI_{50}$) or the concentration of the test compound which reduced by 50% radioactivity specificity fixed to the standard receptor. The $CI_{50}$ for the products of Examples 1 and 3 were 1.8 and 4.9 nanomoles, respectively.

B. In vivo analgesic activity

In the hot plate test, female mice weighing 22 to 24 g were placed individually on a copper plate maintained at 56° C. and the reaction to the pain was manifested by licking of the paws by the animal. The time of this reaction was noted and the mice which did not react in less than 8 seconds were not used. The mice were divided into homogenous groups and the test compound was administered subcutaneously with one group receiving only the vehicle. The reaction time to pain was measured again 30 to 60 minutes after treatment and the dose which increased the reaction time 100% ($DA_{100}$) 30 minutes after treatment as compared to the control animals was determined. The $DA_{100}$ for the compound of Example 1 was 8 mg/kg.

C. Antiarythmic Activity

Tracheotomized male rats weighing 300 to 350 g were anesthesized intraperitonally with 1.20 g/kg of urethane and were subjected to artifical respiration of 40 to 50 insufflations of 3 ml/minute. Needles were implanted subcutaneously to register the electrocardiogram of the rats by the signal of DII derivative. The test compounds were administered intraveinously and 5 minutes later, the jugular veins of the rats were perfused with 10 μg/mn or 0.2 ml of an aconitine solution and the time of appearance of troubles in the cardiac rhythm was noted. The results were expressed as a percentage of the elongation of time of the appearance of the cardiac rhythm troubles as compared to the controls and as a function of the dose of the test compound. The results of the following Table show that the compounds possess a very good antiarythmic properties.

TABLE

| Example | Dose in mg/kg | % elongation of time |
|---|---|---|
| 1 | 10 | +65 |

D. Diuretic Activity

Male rats of the Sprague-Dawley strain weighing 180 to 200 g were fasted for 17 hours before the test but received as much water as they desired. Groups of 8 rats were used for the test doses with the rats receiving the test compound or only the vehicle. The remaining volume was measured hourly for 2 hours after administration of the compound. At the end of this period, the urine was collected and the activity of the compounds was expressed as the percentage of variation calculated as the urinary volume in the period $t_{1h}-t_{2h}$.

| Example | Dose in mg/kg | % Variation |
|---|---|---|
| 1 | 1 | +131 |
| 3 | 1 | +267 |

E. Acute Toxicity

The $LD_0$ or the dose at which there was no mortality after 8 days was determined on mice and the $DL_0$ for the compounds of Examples 1,3 and 4 was 100, 100 and 200 mg/kg, respectively.

Various modifications of the compounds and method of the invention may be made without departing from the spirit or scope thereof and it is to be understood that the invention is intended to be limited only as defined in the appended claims.

What is claimed is:

1. A compound selected from the group consisting of all enantiomeric and diastereoisomeric forms possible of compounds of the formula

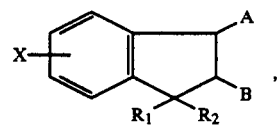

wherein X is selected from the group consisting of hydrogen, halogen, and alkyl and alkoxy of 1 to 5 carbon atoms, $R_1$ and $R_2$ are individually selected from the group consisting of hydrogen and alkyl of 1 to 5 carbon atoms, one of A and B being

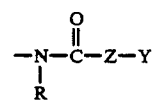

and the other being

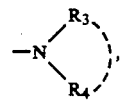

R is hydrogen or alkyl of 1 to 5 carbon atoms, Z is $-(CH_2)_n-$ or branched alkylene of 2 to 8 carbon atoms, n is an integer from 0 to 5, Y is selected from the group consisting of benzofuranyl, benzothienyl or thienyl, $R_3$ and $R_4$ are individually hydrogen or alkyl of 1 to 5 carbon atoms or taken together with the nitrogen form a heterocyclic of 5 to 6 ring members and optionally containing —O—, —D— or nitrogen in the ring or their non-toxic, pharmaceutically acceptable acid addition salts.

2. A compound of claim 1 wherein A and B have trans configuration.

3. A compound of claim 1 wherein R is hydrogen, methyl or ethyl and Z is $-CH_2-$ or

4. A compound of claim 1 wherein X, R₁ and R₂ are hydrogen and

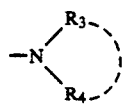

is pyrrolidine.

5. A compound of claim 1 selected from the group consisting of trans (±) N-[2,3-dihydro-2-(1-pyrrolidinyl-1H-inden-1-yl]-N-methyl-4-benzo[b]thiophene-acetamide or its non-toxic, pharmaceutically acceptable acid addition salts.

6. An antiarythmic composition comprising an antiarythmically effective amount of at least one compound of claim 1.

7. A composition of claim 6 wherein in the compound (I) A and B have trans configuration.

8. A composition of claim 6 wherein R is hydrogen, methyl or ethyl and Z is —CH₂— or

9. A composition of claim 6 wherein in the compound (I) X, R₁ and R₂ are hydrogen and

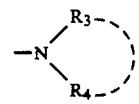

is pyrrolidine.

10. A composition of claim 6 wherein the compound is selected from the group consisting of trans (±) N-[2,3-dihydro-2-(1-pyrrolidinyl-1H-inden-1yl]-N-methyl-4-benzo[b]thiophene-acetamide or its non-toxic, pharmaceutically acceptable acid addition salts.

11. A method of inducing antiarythmic activity in warm-blooded animals comprising administering to warm-blooded animals an antiarythmically effective amount of at least one compound of claim 1.

12. A method of claim 11 wherein in the compound (I) A and B have trans configuration.

13. A method of claim 11 wherein R is hydrogen, methyl or ethyl and Z is —CH₂— or

14. A method of claim 11 wherein in the compound (I) X, R₁ and R₂ are hydrogen and

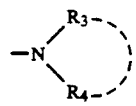

is pyrrolidine.

15. A method of claim 11 wherein the compound is selected from then group consisting of trans (±) N-[2,3-dihydro-2-(1-pyrrolidinyl-1H-inden-1-yl]-N-methyl-4-benzo[b]thiophene-acetamide or its non-toxic, pharmaceutically acceptable acid addition salts.

16. A compound of claim 1 selected from the group consisting of N-[2,3-dihydro-2-(1-pyrrolidinyl)-1H-inden-1-yl]-N-methyl-5-phenyl-2-thiophene-acetamide and its non-toxic, pharmaceutically acceptable acid addition salts.

* * * * *